US00PP18694P2

(12) United States Plant Patent
Klemm

(10) Patent No.: US PP18,694 P2
(45) Date of Patent: Apr. 1, 2008

(54) ***CALIBRACHOA* PLANT NAMED 'KLECA06126'**

(50) Latin Name: *Calibrachoa*
Varietal Denomination: KLECA06126

(76) Inventor: Nils Klemm, Hanfäcker 10, Stuttgart (DE), 70378

( * ) Notice: Subject to any disclaimer, the term of this patent is extended or adjusted under 35 U.S.C. 154(b) by 0 days.

(21) Appl. No.: 11/473,814

(22) Filed: Jun. 23, 2006

(51) Int. Cl.
*A01H 5/00* (2006.01)

(52) U.S. Cl. ..... Plt./263

(58) Field of Classification Search ..... Plt./263, Plt./356

See application file for complete search history.

*Primary Examiner*—Kent Bell
*Assistant Examiner*—June Hwu
(74) *Attorney, Agent, or Firm*—Stratton Ballew PLLC

(57) ABSTRACT

A new and distinct variety of *Calibrachoa* plant named 'KLECA06126', characterized by its double flowers, good branching, and good stress and weather tolerance.

2 Drawing Sheets

Latin name of the genus and species of the plant claimed: *Calibrachoa* sp.
Variety denomination: 'KLECA06126'.

BACKGROUND AND SUMMARY OF THE INVENTION

The present invention relates to a new and distinct *Calibrachoa* hybrid that has been given the name 'KLECA06126'. The claimed plant is the product of a controlled breeding program carried out by the inventor at Stuttgart, Germany. 'KLECA06126' was selected in 2005 from a group of seedlings that were obtained as a result of a cross in 2004 between female parent 'X 436' (unpatented) and male parent 'W 403' (unpatented). Asexual propagation of 'KLECA06126' was carried out in at Stuttgart in 2005 by cutting and by in vitro shoot-tip culture. The characteristics of the claimed plant have been shown to be stable and reproduce true to type through multiple generations of asexual propagation.

'KLECA06126' is distinguished as to novelty by the following characteristics:

1. Double flowers — more than five petals per flower
2. Good branching
3. Foliage resistant to stress and rain The claimed plant is distinguishable from its parents by a number of features, as set forth in Table 1 below.

TABLE 1

| | 'X 436' | 'W 403' | 'KLECA06126' |
|---|---|---|---|
| Flower type | Double | Single | Double |
| Number of petals | More than 5 | 5 | More than 5 |
| Branching | Less branching | Good branching | Good branching |

'KLECA06126' can also be compared with similar variety 'M. F. Pink (S51)' (not patented). The double flower of 'KLECA06126' having more than 5 petals is distinguishable from the single, 5 petal flowers of 'M. F. Pink (S51)'.

DETAILED BOTANICAL DESCRIPTION

Figure 1:
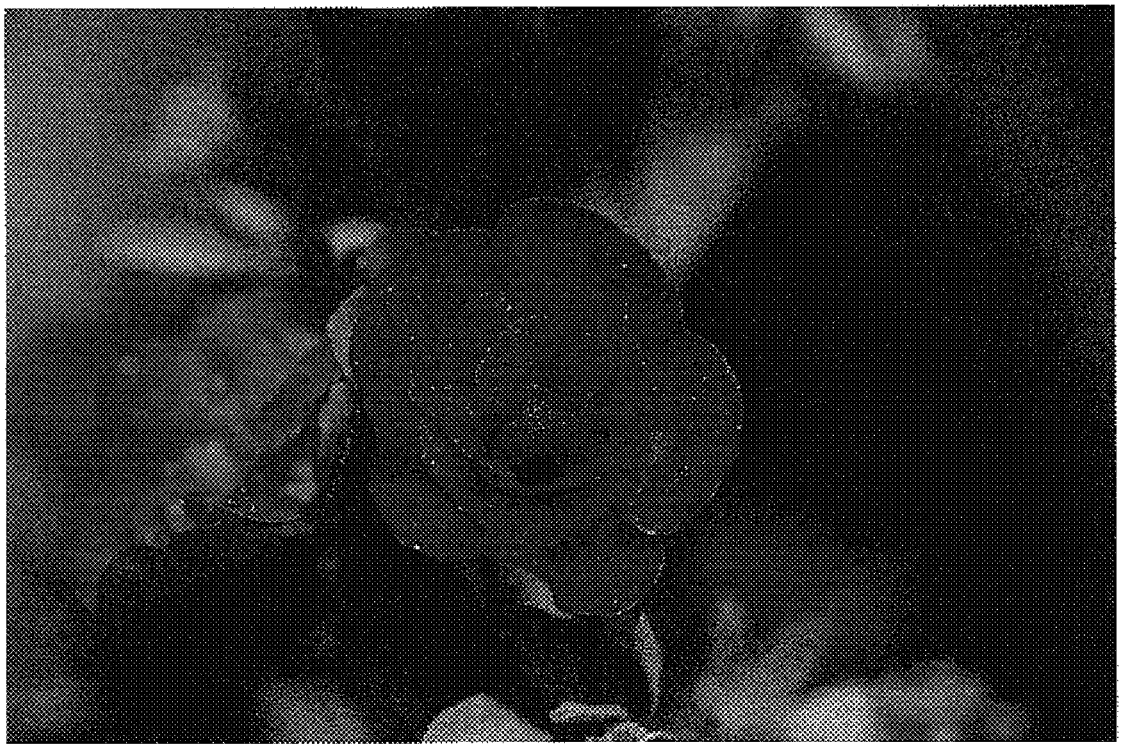
FIG. 1 is a close up illustration of a typical flower of 'KLECA06126'.
Figure 2:
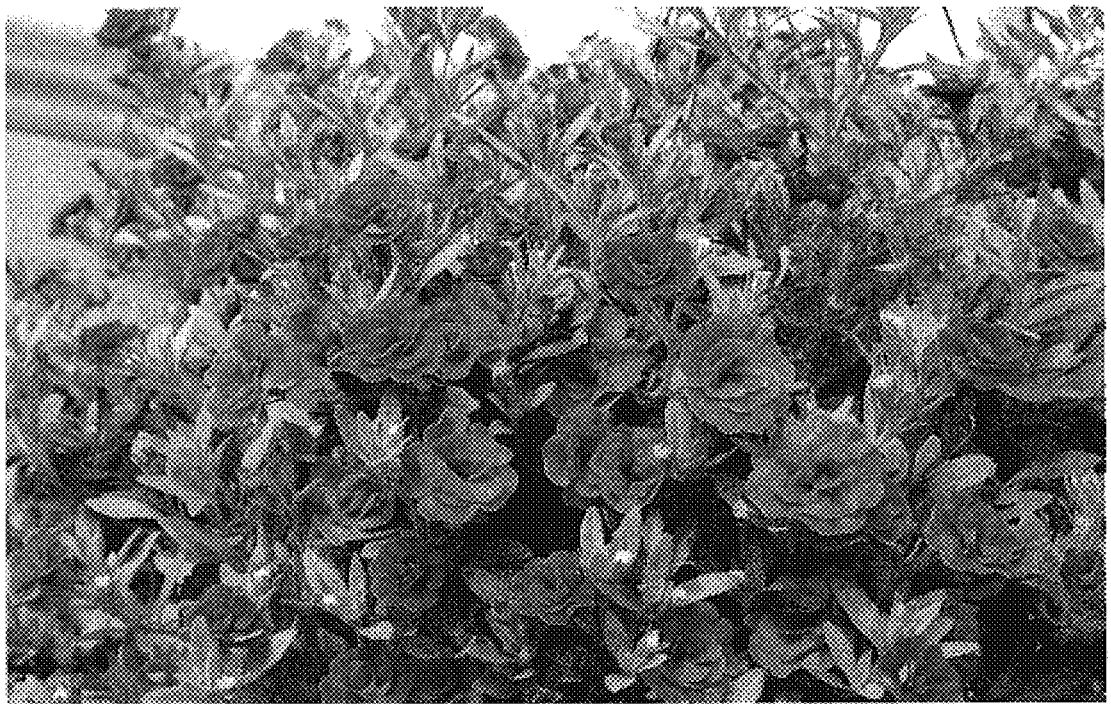
FIG. 2 is an illustration of a typical plant of 'KLECA06126' showing the leaves and flowers of the claimed plant.

The following detailed botanical description is based on observations made during March 2006 at Stuttgart, Germany. The observed plants were approximately five months old, grown in 12 cm plastic pots in a glass-covered greenhouse. All colors are described according to the Royal Horticultural Society Colour Chart. It should be understood that the characteristics described will vary somewhat depending upon fertilization, cultural practices, and climatic conditions, and can vary with location and season. Quantified measurements are expressed as an average of measurements taken from a number of individual plants of the new variety. The measurements of any individual plant, or any group of plants, of the new variety may vary from the stated average.

Plant:
*Type.*—Annual, potted plant.
*Crop time.*—November to March.
*Vigor.*—Medium.
*Overall plant shape.*—Flat to upright.
*Growth habit.*—Trailing.
*Plant height.*—6 cm.
*Branching habit.*—Freely.
*Area of spread.*—20 cm.
*Growth rate.*—Medium.

Branch:
*Basal branching.*—Yes.
*Pinching required.*—No.
*Number of lateral branches.*—5.
*Lateral branch length.*—10 cm.
*Lateral branch diameter.*—2 to 5 mm.
*Internode length.*—0.3 cm to 2.0 cm.
*Stem appearance.*—Dull.

*Stem aspect.*—Flat.
*Stem diameter.*—2 mm to 4 mm.
*Stem strength.*—Weak.
*Stem color.*—Yellow green 145A.
*Stem pubescence.*—Slightly present.

Leaf:
*Arrangement.*—Alternate.
*Leaf blade:*
*Length.*—0.3 cm to 4.0 cm.
*Width.*—0.2 cm to 1.3 cm.
*Shape.*—Lanceolate to elliptic.
*Shape of tip.*—Broad acute.
*Shape of base.*—Attenuated.
*Texture of upper side.*—Leathery.
*Texture of lower side.*—Smooth.
*Color of upper side of young leaf.*—Green 137C.
*Color of under side of young leaf.*—Green 137D.
*Color of upper side of mature leaf.*—Green 137B.
*Color of under side of mature leaf.*—Green 137C.
*Color of upper side of vein.*—Green 144B.
*Color of under side of vein.*—Green 144C.
*Pubescence of upper surface.*—Little.
*Leaf margin.*—Entire.
*Venation pattern.*—Pinnate.
*Petiole length.*—0 cm.
*Durability of foliage.*—Very good; foliage retains healthy appearance when subjected to heat stress, drought stress or physical stress.

Flower:
*Inflorescence type.*—Solitary.
*Flower type.*—Double Flower (more than 5 petals per flower).
*Flowering habit.*—Continuous.
*Quantity of flowers per lateral stem.*—11.
*Quantity of flower buds per lateral stem.*—35.
*Quantity of flowers and buds per plant.*—230.
*Time from planting to bud appearance.*—14–15 weeks.
*Natural flowering season.*—Summertime.
*Time from bud appearance to full bloom.*—5 days.
*Fragrance.*—None.
*Flower bud length.*—1.3 cm.
*Flower bud diameter.*—0.6 cm.
*Flower bud shape.*—Irregular — oblong.
*Flower bud color.*—Yellow green 149C and purple 77C.
*Flower aspect.*—Outward.
*Flower diameter.*—3.5 cm.
*Flower depth.*—2 cm.
*Flower throat diameter.*—1 cm.
*Flower tube length.*—1.6 cm.
*Flower tube diameter.*—0.4 cm.
*Flower longevity on plant.*—7 days, persistent.
*Petal appearance.*—Satiny.
*Petal arrangement.*—Radial symmetric.
*Petal number.*—8 to 12.
*Petal shape.*—Reniform to heart shaped.
*Petal margin.*—Entire.
*Petal tip.*—Rounded to emarginate.
*Petal length from throat.*—1.5 cm to 2.0 cm.
*Petal width.*—0.8 cm to 1.5 cm.
*Petal texture, upper side.*—Smooth.
*Petal texture, lower side.*—Smooth.
*Throat texture.*—Smooth.
*Tube texture.*—Smooth.
*Petal color when opening, upper side.*—Red purple 74B.
*Petal color when opening, under side.*—Purple 77C.
*Petal color fully open, upper side.*—Red purple 74B.
*Petal color fully open, under side.*—Purple 77C.
*Petal color, fading to.*—Red purple 74B.
*Flower tube color.*—Green yellow 1B.
*Flower throat color.*—Purple 77A.
*Vein color, upper side of petals.*—Red purple 74B.
*Vein color, under side of petals.*—Purple 77A.
*Vein color, throat.*—Purple 77A.
*Vein color, tube.*—Purple 77A.
*Petaloid appearance.*—Satiny.
*Petaloid arrangement.*—Radial symmetric.
*Number of petaloids.*—Usually 1 to 4.
*Petaloid shape.*—Lanceolate.
*Petaloid margin.*—Entire.
*Petaloid length.*—2 to 8 mm.
*Petaloid width.*—1 to 3 mm.
*Petaloid texture, upper side.*—Smooth.
*Petaloid texture, under side.*—Smooth.
*Petaloid color immature.*—Red purple 74C.
*Petaloid color, mature.*—Red purple 74D.

Sepal:
*Appearance.*—Glossy.
*Arrangement.*—Rosette.
*Length.*—1.8 cm.
*Width.*—0.5 cm.
*Texture, upper side.*—Smooth.
*Texture, lower side.*—Smooth.
*Number.*—5.
*Shape.*—Lanceolate to elliptic.
*Margin.*—Entire.
*Tip.*—Acute.
*Base.*—Open.
*Color, upper side.*—Green 138A.
*Color, under side.*—Green 138B.
*Calyx shape.*—Funnel.

Peduncle:
*Length.*—1 cm to 2 cm.
*Diameter.*—0.2 cm.
*Angle.*—Erect, 75°.
*Strength.*—Typical for *Calibrachoa* sp.
*Texture.*—Smooth.
*Color.*—Yellow green 145A.
*Stamens present.*—Some, typically 0 to 3 depending on temperature.

Anther:
*Shape.*—Elliptic.
*Size.*—1 mm.
*Color.*—Yellow green 145A.

Pollen:
*Amount.*—Little.
*Color.*—Yellow green 154C.

Pistil:
*Presence.*—1, sometimes more than 1.
*Length.*—0.5 cm.

Stigma:
*Shape.*—Ovate.
*Color.*—Yellow green 145A.

Ovary:
*Color.*—Yellow green 145A.

Style:
*Length.*—0.4 cm.
*Color.*—Yellow green 145A.

Other flowering characteristics: Double Flowering Type.
Drought tolerance: Very Good.
Weather tolerance: Good.
Disease resistance: Typical for *Calibrachoa* sp.

I claim:

1. A new and distinct variety of *Calibrachoa* plant, substantially as illustrated and described herein.

* * * * *